(12) United States Patent
Kim

(10) Patent No.: US 11,752,260 B2
(45) Date of Patent: *Sep. 12, 2023

(54) FLOW RATE CONTROL DEVICE FOR SUPPLYING LIQUID CHEMICAL

(71) Applicant: S&SMED CO., LTD., Anyang-si (KR)

(72) Inventor: Kiwoon Kim, Gyeonggi-do (KR)

(73) Assignee: S&SMED CO., LTD.

( * ) Notice: Subject to any disclaimer, the term of this patent is extended or adjusted under 35 U.S.C. 154(b) by 367 days.

This patent is subject to a terminal disclaimer.

(21) Appl. No.: 17/088,576

(22) Filed: Nov. 3, 2020

(65) Prior Publication Data

US 2021/0052810 A1    Feb. 25, 2021

Related U.S. Application Data

(63) Continuation of application No. 15/935,454, filed on Mar. 26, 2018, now Pat. No. 10,850,030.

(30) Foreign Application Priority Data

Jul. 24, 2017   (KR) ........................ 10-2017-0093300

(51) Int. Cl.
*A61M 5/168*     (2006.01)
*A61M 5/14*      (2006.01)

(52) U.S. Cl.
CPC ...... *A61M 5/16809* (2013.01); *A61M 5/1413* (2013.01); *A61M 5/16804* (2013.01); *A61M 5/16877* (2013.01); *A61M 5/16881* (2013.01)

(58) Field of Classification Search
CPC .... A61M 5/14; A61M 5/168; A61M 2205/33; A61M 2205/331; A61M 5/16804;

(Continued)

(56) References Cited

U.S. PATENT DOCUMENTS

| 4,537,680 | A * | 8/1985 | Barth ..................... B01D 29/44 210/498 |
| 6,231,770 | B1 * | 5/2001 | Bormann ............. B01D 63/082 210/420 |

(Continued)

FOREIGN PATENT DOCUMENTS

| ES | 2167281 A1 * | 5/2002 | ........ A61M 5/16877 |
| ES | 2167281 A1 | 5/2002 | |

(Continued)

*Primary Examiner* — Jason E Flick
(74) *Attorney, Agent, or Firm* — Renaissance IP Law Group LLP

(57) ABSTRACT

Provided is a flow rate control device for supplying liquid chemicals. The device according to an embodiment of the present disclosure includes a housing unit which is placed at the location from which liquid chemicals are supplied and comprises an inflow conduit on one side to which the liquid chemicals flow in and an outflow conduit from which the flowed-in liquid chemicals whose flow rate is controlled flow out; and a control unit which is integrated with the housing unit and comprises an inflow space which comes in contact with an inflow hole at a terminal portion of the inflow conduit, an outflow space which comes in contact with an outflow hole at a terminal portion of the outflow conduit and a control path which is connected between the inflow space and the outflow space to control the flow rate of the flowed-in liquid chemicals, wherein the control path has a controlled inner diameter and a controlled length according to the flow rate a use r aims at.

6 Claims, 6 Drawing Sheets

(58) Field of Classification Search
CPC ............ A61M 5/16877; A61M 5/1413; A61M 5/16809; A61M 5/16881; A61M 2205/3334; A61M 2005/1652; A61M 39/10; A61M 2039/1077; A61M 2039/1083; A61M 2039/1094; A61M 39/12; A61M 39/14
See application file for complete search history.

(56) References Cited

U.S. PATENT DOCUMENTS

| | | |
|---|---|---|
| 7,661,440 B2 | 2/2010 | Mabry et al. |
| 8,337,701 B2 * | 12/2012 | Martin .................. A61M 5/165 96/6 |
| 2001/0021830 A1 | 9/2001 | Yamada et al. |
| 2010/0057015 A1 | 3/2010 | Lee |
| 2015/0343140 A1 | 12/2015 | Khalaj et al. |

FOREIGN PATENT DOCUMENTS

| | | |
|---|---|---|
| JP | 2012192178 A | 10/2012 |
| KR | 20000010499 A | 2/2000 |

* cited by examiner

FLOW RATE CONTROL DEVICE FOR SUPPLYING LIQUID CHEMICAL

BACKGROUND OF THE DISCLOSURE

Field of the Disclosure

The present disclosure relates to a flow rate control device for supplying liquid chemicals, more particularly a flow rate control device for liquid chemicals which enhances flow rate control efficiency by improving the structure which controls the flow rate of liquid chemicals when the liquid chemicals are supplied, thereby minimizing the installation area and by extending the diameter of a flow path according to flow rate controls, thereby minimizing obstruction in the flow path by particles as foreign object.

Description of the Background Art

Generally a patient cannot take in food due to problems of their digestive functions and is injected through their blood vessels with necessary nutrients such as glucose. Various liquid chemicals such as antitumor agents, antibiotics, analgesics and the like are also injected into such patients through their blood vessels for treating their diseases.

Here, it is desirable to inject such nutrients and/or liquid chemicals through their blood vessels in accurate supply quantities and according to predetermined flow rates depending on the state of the patient.

In particular, antibiotics to be administered to critically ill patients who suffer from cancer, leukemia and the like, different from ordinary liquid chemicals, should be supplied, taking into account the nature of such medicine, in infinitesimal quantities at a steady rate. Likewise, analgesics to be administered to patients who suffer from persistent pain after surgery to mitigate the pain should be supplied in appropriate quantities at an identical interval.

Such critically ill patients can experience abnormal symptoms such as shock, temporary hypertension, vessel wall damage and the like when they undergo a change in the liquid chemicals they are injected with in terms of supply quantities or flow rates which lead to the interval of administration.

Therefore, such a flow rate control device for controlling the flow rate of the supplied liquid chemicals, thereby preventing any change in the flow rate is installed and used at the location to which such chemicals are supplied.

Such a flow rate control device for supplying liquid chemicals according to an existing technology is installed at the location to which such chemicals are supplied. Such a flow rate control device has capillary tubes with a fine diameter and a length for achieving a predetermined flow rate and installed at the location to which liquid chemicals pass through so that the liquid chemicals, whose flow rates are controlled when the chemicals pass through the capillary tubes, are supplied.

As described thus far, the flow rate control device for supplying liquid chemicals according to an existing technology controls its flow rate by flowing the liquid chemicals through a plurality of the fine capillary tube. The length of the capillary tubes of such a flow rate control device is determined according to the degree of the flow rate. It is difficult to manufacture such capillary tubes since the capillary tubes should have an infinitesimal hole with high degree of linearity so as to minimize any change in flow rates. Furthermore, since such holes have an infinitesimal diameter, there is a limit to extending the length of the capillary according to decrease in flow rates.

Even after being filtered with an appropriate filter, liquid chemicals which react with each other can produce particles as foreign object if temperature changes and time for administration is extended. Since the flow rate control device for supplying liquid chemicals according to an existing technology has the capillary tubes having an infinitesimal hole, such produced particles can obstruct the hole when they attempt to pass through the hole making supply of the liquid chemicals stop, which requires frequent inspection and replacement.

SUMMARY OF THE DISCLOSURE

To resolve the problems, the present disclosure provides the flow rate control device for supplying liquid chemicals which enhances flow rate control efficiency by improving the structure which controls the flow rate of liquid chemicals when the liquid chemicals are supplied, thereby minimizing the installation area and by extending the diameter of a flow path according to flow rate controls, thereby minimizing obstruction in the flow path by particles as foreign object.

The present disclosure is not limited to the objectives described above. Other undescribed objectives should be understandable in the following description.

To achieve the objectives, the present disclosure provides the flow rate control device for supplying liquid chemicals including:

a housing unit which is placed at the location from which liquid chemicals are supplied and includes an inflow conduit on one side to which the liquid chemicals flow in and an outflow conduit from which the flowed-in liquid chemicals whose flow rate is controlled flow out; and a control unit which is integrated with the housing unit and includes an inflow space which comes in contact with an inflow hole at a terminal portion of the inflow conduit, an outflow space which comes in contact with an outflow hole at a terminal portion of the outflow conduit and a control path which is connected between the inflow space and the outflow space to control the flow rate of the flowed-in liquid chemicals, wherein the control path has a controlled inner diameter and a controlled length according to the flow rate a user aims at.

The housing unit can further include an insertion protrusion which protrudes from one side so that the housing unit is fastened to the control unit, has a control space in which the control path of the control unit is inserted and has a leak prevention groove on another side which assumes the shape of a groove and is inserted into the control unit so that hermeticity is maintained.

The control unit can include:

a control frame having a housing accepting groove along the outer circumference around the control path, which assumes the shape of a groove, into which the protruding portion of the housing unit is inserted so that the housing unit is secured in order to prevent the liquid chemicals supplied via the control path from being leaked; and a leak prevention protuberance which protrudes from inside the housing accepting groove and is inserted into and integrated with the housing unit in order to prevent the liquid chemicals through the control path from being leaked outside.

The control path can be arranged so that the inflow hole and the outflow hole are connected thereto and placed in a zigzag pattern so that the flow path having a predesigned diameter for the flowed-in liquid chemicals to flow at a prespecified flow rate is formed up to a predesigned length.

Inside the control frame, the inflow space to which the liquid chemicals flow in from the housing unit can be formed; the control path is formed from the inflow space via an inflow transport path in a zigzag way to control flow rates; and the outflow space is formed off which the liquid chemicals flow out to the housing unit from the control path via an outflow transport path.

The flow rate control device for supplying liquid chemicals can further include inflow staining protuberances which protrude at a plurality of sites so that a plurality of inflow passing paths are formed inside the inflow transport path at a predetermined interval and filter particles contained in the liquid chemicals transported from the inflow transport path in order to remove the particles.

The flow rate control device for supplying liquid chemicals can further include outflow straining protuberances which protrude at a plurality of sites so that a plurality of outflow passing paths are formed inside the outflow transport path at a predetermined interval and filter particles contained in the liquid chemicals transported from the outflow transport path in order to remove the particles.

Meanwhile, another embodiment of the present disclosure provides the flow rate control device for supplying liquid chemicals including:

the housing unit which is placed at the location from which the liquid chemicals are supplied and has the inflow conduit on one side to which the liquid chemicals flow in and the outflow conduit from which the flowed-in liquid chemicals whose flow rate is controlled flow out;

a flow rate control unit which is integrated with the housing unit and includes a control inflow space which comes in contact with the inflow hole at the terminal portion of the inflow conduit, a control outflow space which comes in contact with the outflow hole at the terminal portion of the outflow conduit and a flow rate control path which is connected between the control inflow space and the control outflow space to control the flow rate of the flowed-in liquid chemicals; and a control support unit which is integrated with the housing and has the flow rate control unit so that the flow rate control unit is inserted and supported inside the control support unit and keeps hermeticity between the housing unit and the flow rate control unit itself, wherein the flow rate control path has a controlled inner diameter and a controlled length according to the flow rate a user aims at.

The housing unit can further include the insertion protrusion which protrudes from one side so that the housing unit is fastened to the control unit, has the control space in which the control path of the control unit is inserted and has the leak prevention groove on another side which assumes the shape of a groove and is inserted into the control unit so that hermeticity is maintained.

The flow rate control unit can have a flow rate control frame inside the flow rate control unit along the outer circumference of the flow rate control path so that hermeticity is maintained between the housing unit and the control support unit while the flow rate control path can be arranged so that the inflow hole and the outflow hole are connected thereto and placed in a zigzag pattern so that the flow path having a predesigned diameter for the flowed-in liquid chemicals to flow at a prespecified flow rate is formed up to a predesigned length.

Inside the flow rate control frame, the control inflow space to which the liquid chemicals flow in from the housing unit can be formed; the flow rate control path is formed from the control inflow space via a control inflow transport path in a zigzag way to control flow rates; and the control outflow space is formed off which the liquid chemicals flow out to the housing unit from the flow rate control path via a control outflow transport path.

The flow rate control device for supplying liquid chemicals can further include control inflow staining protuberances which protrude at a plurality of sites so that a plurality of control inflow passing paths are formed inside the control inflow transport path at a predetermined interval and filter particles contained in the liquid chemicals transported from the control inflow transport path in order to remove the particles.

The flow rate control device for supplying liquid chemicals can further include control outflow straining protuberances which protrude at a plurality of sites so that a plurality of control outflow passing paths are formed inside the control outflow transport path at a predetermined interval and filter particles contained in the liquid chemicals transported from the control outflow transport path in order to remove the particles.

In addition, the control support unit includes:

a support frame which is integrated with a housing frame and has a control insertion space inside which the flow rate control unit is inserted and kept hermetic and a support insertion groove into which the insertion protrusion which encircles the control insertion space is inserted; and a support protuberance which protrudes from the insertion protrusion to be inserted into the leak prevention groove inside the support frame.

The flow rate control device for supplying liquid chemicals according to an embodiment of the present disclosure provides advantageous effects of minimizing the installation area by improving the structure of controlling liquid chemical flow rates at the time of supplying such liquid chemicals and minimizing obstruction by particles as foreign object by extending the diameter of the flow path according to flow rate controls, thereby enhancing flow rate control efficiency.

The flow path for controlling liquid chemical flow rates of the flow rate control device for supplying liquid chemicals according to an embodiment of the present disclosure is formed in a zigzag pattern, which provides advantageous effects of minimizing particle obstruction in the liquid chemicals and minimizing an area according to transport distance, thereby enhancing flow rate control efficiency.

In addition, the flow path of the flow rate control device for supplying liquid chemicals according to an embodiment of the present disclosure provides an advantageous effect of enhancing flow rate control efficiency by minimizing particle obstruction because it supplies the liquid chemicals with such particles contained in it filtered out by having a plurality of protuberances for removing the particles at a predetermined interval.

DETAILED DESCRIPTION OF THE DISCLOSURE

Figure 1:
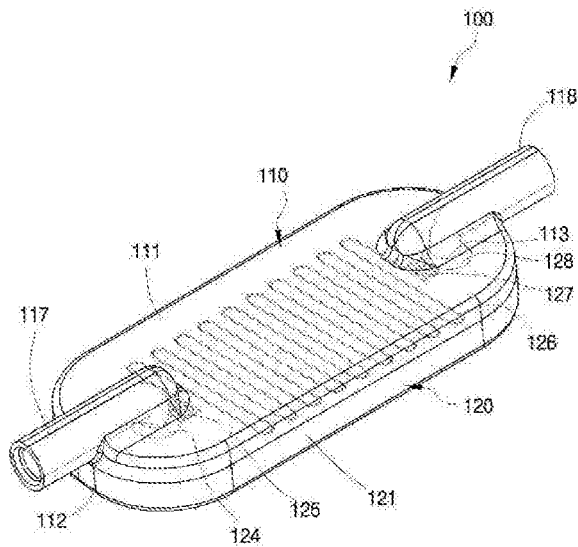
FIG. 1 is an oblique view which describes the flow rate control device for supplying liquid chemicals according to an embodiment of the present disclosure.

Since the present disclosure may have various modifications and embodiments, the present disclosure is now described below in detail in connection with specific embodiments and accompanying drawings. However, it does not intend to limit the present disclosure to specific embodiments and must be acknowledged that the embodiments should include all the modifications, equivalents and substitutes within the technical thoughts and scope of the present disclosure. Reference numerals similar to each other are used to denote subject matters also similar to each other in the accompanying drawings.

Terms such as first, second, A, B, etc. may be used to denote various subject matters but the subject matter must not be restricted by means of the terms.

Such terms are used in order only to differentiate a subject matter from other subject matters. For example, not deviating from the claim scope of the present disclosure, a first subject matter may be designated as second subject matter and vice versa. The term of "and/or" includes a certain item in two or more related and specified items or the combination thereof.

When it is stated that a certain subject matter is "connected" or "linked" to another subject matter, it should be interpreted that the former may be directly connected or linked to the latter but there may be a still another subject matter in between. On the contrary, when it is stated that a subject matter is "directly connected" or "directly linked" to another subject matter, it should be interpreted that there is not any third subject matter in between.

Terms used in this Specification are just to describe specific embodiments and are not intended to set limits to the present disclosure. A singular term includes plurality unless otherwise indicated in another way contextually. The terms of "include/includes/including", "have/has/having", etc. must be interpreted to state that there exist, as laid down in this Specification, feature(s), number(s), phase(s), movement(s), component(s) or part(s) or combination thereof and not to preliminarily exclude any possibility of existence or addition of one or more of those features, number(s), phase(s), movement(s), component(s) or part(s) or combination thereof.

Each of all the terms, including technical or scientific ones, used in this Specification has a sense identical to what is generally understood by a person zo skilled in the art of the present disclosure. Each of terms such as ones defined in common dictionaries should be interpreted to have a sense identical to what is contextually used in the related technology and, unless otherwise clearly defined in this Specification, is not to be interpreted in an ideal or excessively formal way. Embodiments of the present disclosure will be described in more detail hereinafter with reference to the accompanying drawings.

Figure 2:
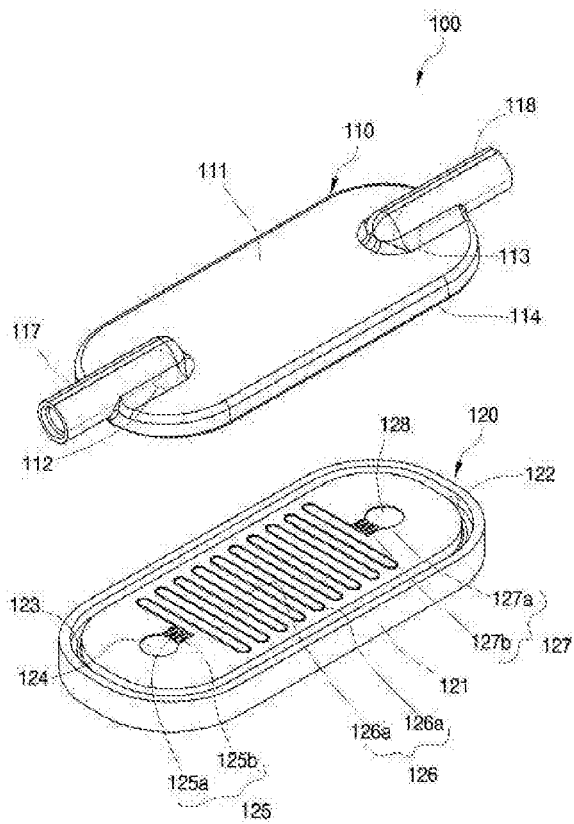
FIG. 2 is a disassembled oblique view which describes the flow rate control device for supplying liquid chemicals of FIG. 1.
Figure 3:
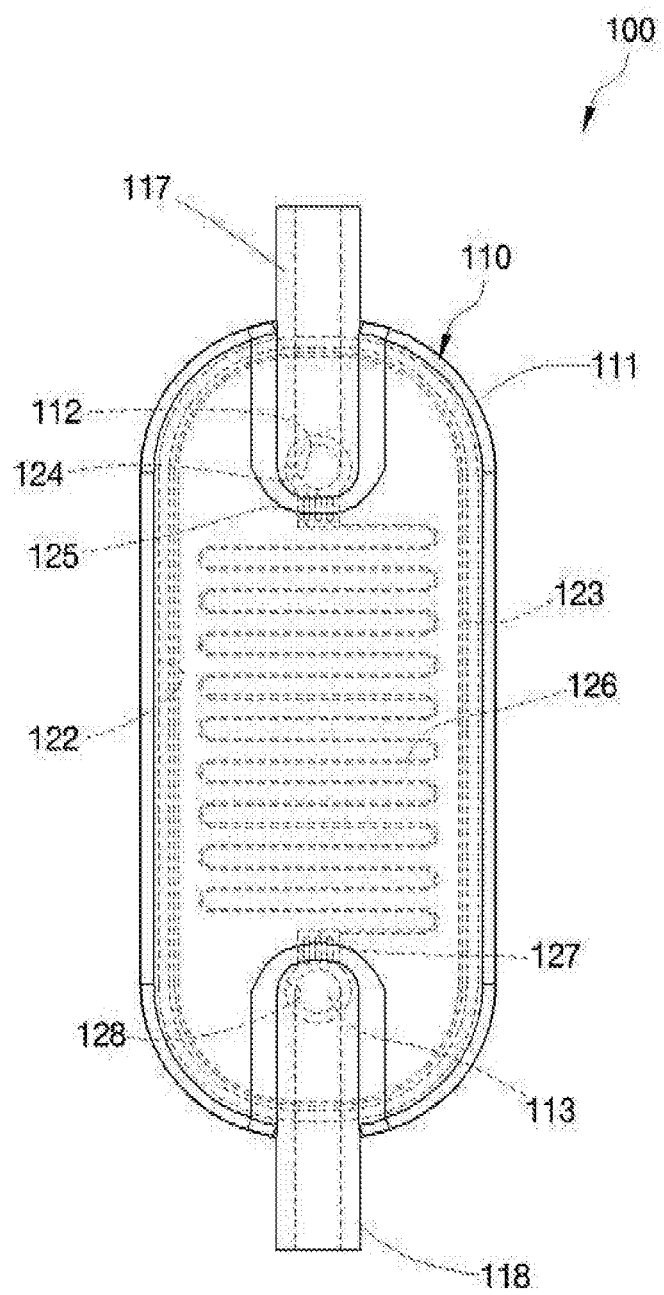
FIG. 3 is a top view which describes the flow rate control device for supplying liquid chemicals of FIG. 1.
Figure 4:
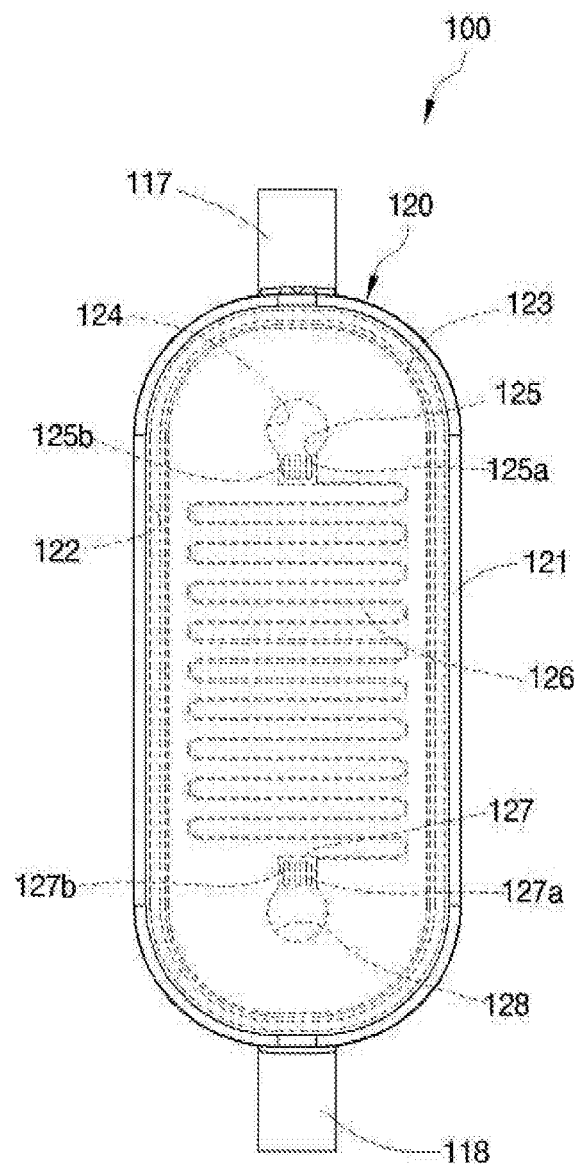
FIG. 4 is a bottom view which describes the flow rate control device for supplying liquid chemicals of FIG. 1.
Figure 5:
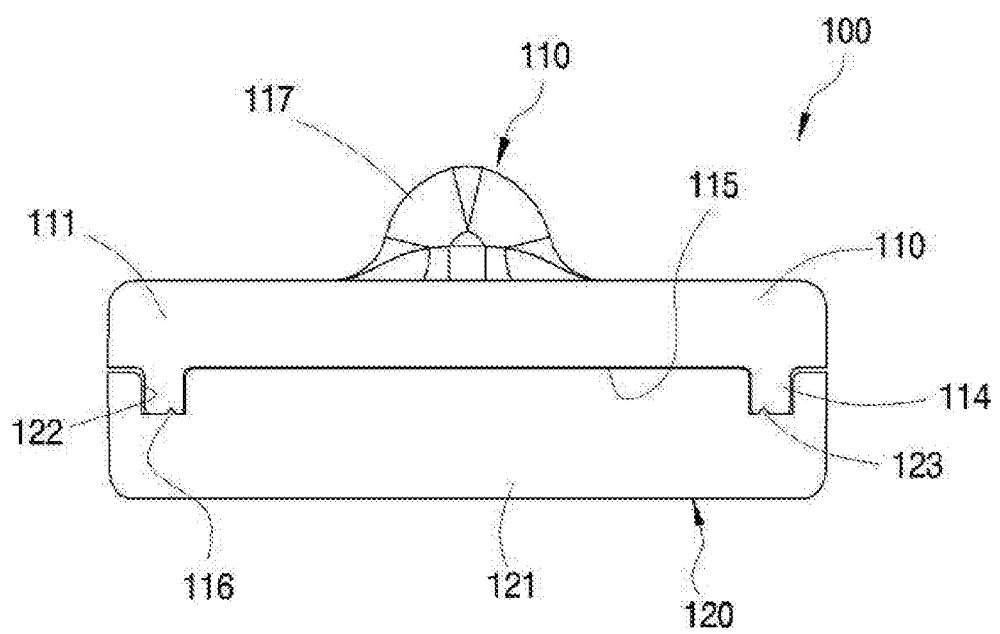
FIG. 5 is a partial cross-sectional view which describes the flow rate control device for supplying liquid chemicals of FIG. 1.

FIG. 1 is an oblique view which describes the flow rate control device for supplying liquid chemicals according to an embodiment of the present disclosure; FIG. 2 is a disassembled oblique view which describes the flow rate control device for supplying liquid chemicals of FIG. 1; FIG. 3 is a top view which describes the flow rate control device for supplying liquid chemicals of FIG. 1; FIG. 4 is a bottom view which describes the flow rate control device for supplying liquid chemicals of FIG. 1; and FIG. 5 is a partial cross-sectional view which describes the flow rate control device for supplying liquid chemicals of FIG. 1.

Referring to FIGS. 1 through 5, the flow rate control device for supplying liquid chemicals 100 according to an embodiment of the present disclosure is an apparatus which is connected between a storage for storing liquid chemicals and a needle for injecting the liquid chemicals into the blood vessels of a patient and controls flow rates of the liquid chemicals so that supply quantities of the liquid chemicals are adjusted in order to treat diseases.

The flow rate control device for supplying liquid chemicals 100 includes the housing unit 110 which transports the liquid chemicals with their flow rates are controlled from their storage to the needle for injecting them and the control unit 120.

The housing unit 110 includes the housing frame 111 which is installed to receive and leak the liquid chemicals, the insertion protrusion 114, the inflow conduit 117 and the outflow conduit 118.

The housing frame 111 is placed between the instrument for storing the liquid chemicals and needle for injecting the liquid chemicals at a location where the housing frame can control flow rates of the liquid chemicals. The housing frame 111 has a width and a length identical to those of the control unit 120 which is integrated with the housing frame 111 to control flow rates of the liquid chemicals and is integrated with the control unit 120 so that the liquid chemicals pass through their inside.

The housing frame 111 has on one side the through-hole shaped inflow hole 112 which receives the liquid chemicals from the instrument for storing the liquid chemicals and supplies the liquid chemicals to the control unit 120 which controls the flow rates.

The housing frame 111 has on the other side has the outflow hole 113 which is connected with the needle for injecting the liquid chemicals so that the liquid chemicals whose flow rate is controlled through the control unit 120 enter the needle.

The insertion protrusion protrudes for the control unit 120 of the housing frame 111 to be inserted when it is integrated. The insertion protrusion has the control space 115 within itself into which a flow rate-controlling part of the control unit 120 is inserted. The insertion protrusion 114 has the leak prevention groove 116 on the side where the control unit 120 is inserted in order to keep hermeticity when the control unit 120 is inserted.

The inflow conduit 117 is placed on one side of one surface of the housing frame 111 at the location where it is linked to the inflow hole 112 to be connected with the liquid chemical storing instrument from which the liquid chemicals are supplied so that the liquid chemicals flow into the location at which the control unit 120 is placed.

The outflow conduit 118 is on the other side of the surface of the housing frame 111 at the location where it is linked to the outflow hole 113 and the liquid zo chemicals whose flow rates have been controlled in the control unit 120 enter the needle.

The control unit 120 includes the control frame 121 which is placed on the opposite surface of the housing frame 111 for controlling flow rates and the leak prevention protuberances 123.

The control frame 121 is placed on the opposite surface of the housing frame 111 and has the control path 126 which is connected with the inflow conduit 117 and the outflow conduit 118 flowing the liquid chemicals through itself for controlling their flow rates. The control path 126 receives the liquid chemicals from the inflow conduit 117 and transports them into the outflow conduit 118 making the liquid chemicals controlled in terms of their flow rates when they pass through the control path 126. To form the control path 126, the flow path having a predetermined width is longitudinally stacked up a plurality of times in a zigzag pattern up to a certain length determined according to a controlled flow rate, where both of the ends in the latitudinal direction are connected alternately into a single flow path.

Within the control frame 121 is inserted the housing accepting groove 122 into which the insertion protrusion 114 is inserted in order to prevent leak of the liquid chemicals.

The control path 126 is formed in a zigzag pattern and includes linear parts 126a which assume the shape of a line and connecting curved parts 126b which are alternately connected to each other at the both ends. Here, a plurality of the linear parts 126a are formed, which have a predetermined inner diameter and placed in a semicircular groove at a predetermined interval. A pair of the connecting curved parts 126b are formed at the ends of the width of each of the linear parts 126a alternately to construct a single path.

In the control path 126 formed in a zigzag pattern, one of the linear parts 126a is connected with a pair of the connecting curved parts 126b to form a single path in order to control the flow rates, where the linear parts 126a are selected up to the very number for making a predetermined total length taking into consideration its inner diameter.

As described above, on one inner side of the control frame 121 is formed the inflow space 124 which is a storage space for storing the liquid chemicals flowing in the location where the inflow hole 112 of the housing frame 111 is. On the other side of the inflow space 124 is formed the inflow transport path 125 which assumes the shape of a flow path in order to transport the flowed-in liquid chemicals to the control path 126.

In other words, the liquid chemicals stored in the instrument for storing the liquid chemicals flow in through the inflow conduit 117 and the inflow hole 112, are temporarily stored in the inflow space 124 and then are transported to the control path 126 for controlling their flow rates through the inflow transport path 125 formed on the other side.

Here, within the inflow transport path 125 is formed the inflow straining protuberances 125a which protrude from the side that is in the direction of the housing frame 111 at a predetermined interval in order to form the inflow passing paths 125b through which the liquid chemicals pass. The inflow straining protuberances 125a are configured so that the particles as foreign object in the liquid chemicals are filtered by one of a plurality of the inflow passing paths 125b and that the rest of the particles are filtered by the rest of the inflow passing paths 125b when the liquid chemicals pass through the inflow passing paths 125b. The inflow straining protuberances 125a are provided in order to remove any particles which can be produced in the liquid chemicals temporarily stored in the inflow space 124.

In other words, the inflow straining protuberances 125a protrude forming a plurality of the inflow passing paths 125b, the liquid chemicals are supplied with the particles contained in them removed in each of the inflow passing paths 125b, thereby limiting obstruction.

On the other side of the control path 126 is formed the outflow transport path 127 through which the liquid chemicals whose flow rate has been controlled are transported while on the other side of the outflow transport path 127 is formed the outflow space 128, which is located at the outflow hole 113 of the housing frame 111 and temporarily stores the liquid chemicals at the location where the liquid chemicals whose flow rate has been controlled are leaked.

Here, the outflow transport path 127 has inside the outflow transport path 127, on the side that is in the direction of the housing frame 111, the outflow straining protuberances 127a at a plurality of sites at a predetermined interval so that the outflow transport path 127 has the outflow passing path 127b through which the liquid chemicals pass. The outflow straining protuberances 127a are configured so that the particles as foreign object contained in the liquid chemicals transported from the outflow transport path 127 are filtered by one of the outflow passing paths 127b and that the rest of the particles are filtered by the rest of the outflow passing paths 127b when the liquid chemicals are transported.

The leak prevention protuberance 123, being placed on one inner side of the control frame 121, protrudes within the housing accepting groove 122 and is inserted into the leak prevention groove 116. The leak prevention protuberance 123 is inserted into the leak prevention groove 116 when the control frame 121 is inserted in the housing frame 111, thereby preventing the liquid chemicals from being leaked outside.

Figure 6:
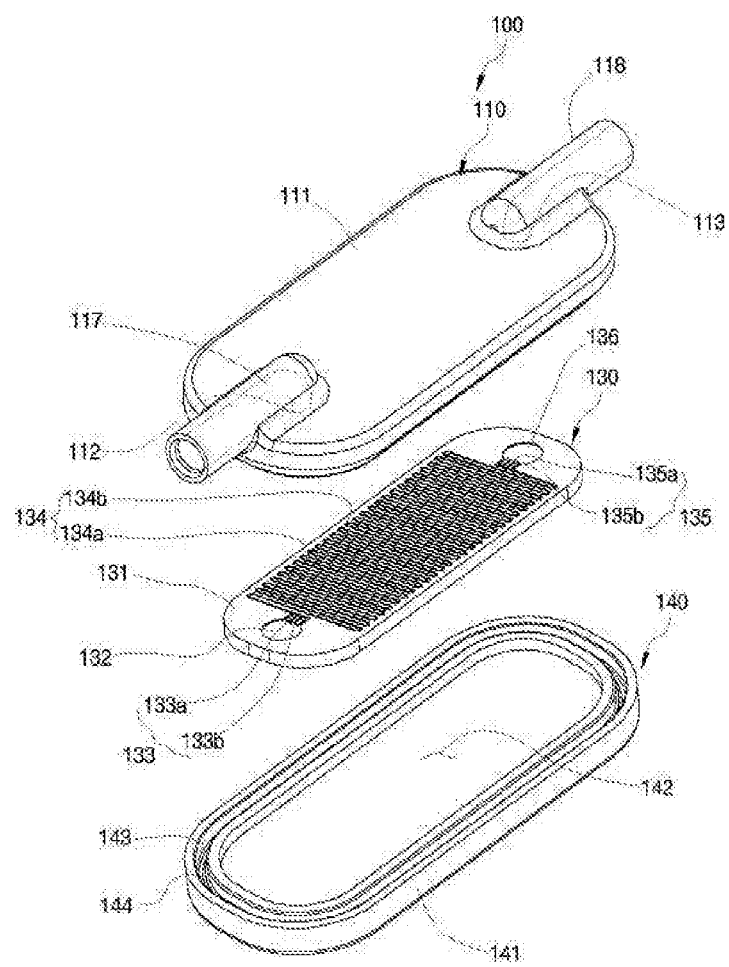
FIG. 6 is a disassembled oblique view which describes the flow rate control device for supplying liquid chemicals according to another embodiment of the present disclosure.
Figure 7:
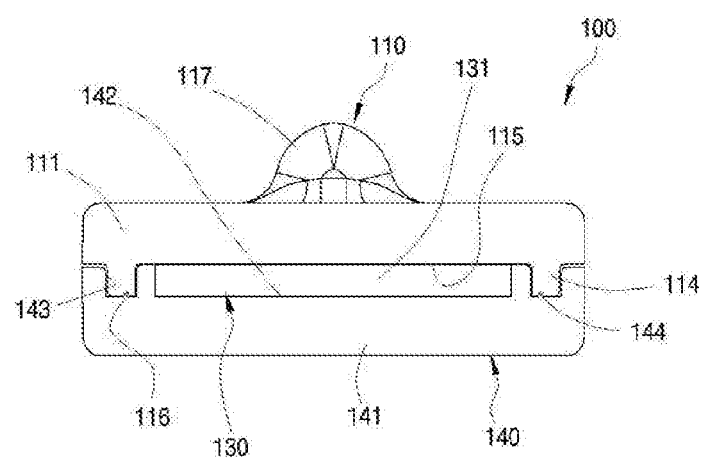
FIG. 7 is a partial cross-sectional view which describes the flow rate control device for supplying liquid chemicals of FIG. 6.

FIG. 6 is a disassembled oblique view which describes the flow rate control device for supplying liquid chemicals according to another embodiment of the present disclosure and FIG. 7 is a partial cross-sectional view which describes the flow rate control device for supplying liquid chemicals of FIG. 6.

Referring now to FIGS. 6 and 7, the flow rate control device for supplying liquid chemicals 100 according to another embodiment of the present disclosure includes the housing unit 110, the flow rate control unit 130 and the control support unit 140. Since the housing unit 110 is identical to that of the flow rate control device for supplying liquid chemicals 100 as described in FIGS. 1 through 5, description of it is omitted but the flow rate control unit 130 and the control support unit 140, which differ, will be described.

The flow rate control unit 130 has the flow rate control frame 131 which is placed on one side of the housing frame 111 so as to control flow rates.

The flow rate control frame 131 is placed on one side of the housing frame 111 and has the flow rate control path 134 which is connected to the inflow conduit 117 and the outflow conduit 118 to control flow rates when the liquid chemicals pass through the flow rate control path 134. The liquid chemicals transported from the inflow conduit 117 are controlled in terms of their flow rates when they pass through the flow rate control path 134 and discharge into the outflow conduit 118. To form the flow rate control path 134, the flow path having a predetermined width is longitudinally stacked up a plurality of times in a zigzag pattern up to a certain length determined according to a controlled flow rate, where both of the ends in the latitudinal direction are connected alternately into a single flow path.

The flow rate control frame 131 is inserted into the control support unit 140 and controls flow rates of the liquid chemicals when the housing frame 111 and the control support unit 140 is integrated for maintaining hermeticity.

The flow rate control path 134 is formed in a zigzag pattern and includes control linear parts 134a which assume the shape of a line and control connecting curved parts 134b which are alternately connected to each other at the both ends. Here, a plurality of the control linear parts 134a are formed, which have a predetermined inner diameter and placed in a semicircular groove at a predetermined interval. A pair of the control connecting curved parts 134b are formed at the ends of the width of each of the control linear parts 134a alternately to construct a single path.

In the flow rate control path 134 formed in a zigzag pattern, one of the control linear parts 134a is connected with a pair of the control connecting curved parts 134b to form a single path in order to control the flow rates, where the control linear parts 134a are selected up to the very number for making a predetermined total length taking into consideration its inner diameter.

As described above, on one inner side of the flow rate control frame 131 is formed the control inflow space 132 which is a storage space for storing the liquid chemicals flowing in the location where the inflow hole 112 of the housing frame 111 is. On the other side of the control inflow space 132 is formed the control inflow transport path 133 which assumes the shape of a flow path in order to transport the flowed-in liquid chemicals to the flow rate control path 134.

In other words, the liquid chemicals stored in the instrument for storing the liquid chemicals flow in through the inflow conduit 117 and the inflow hole 112, are temporarily stored in the inflow space 124 and then are transported to the flow rate control path 134 for controlling their flow rates through the control inflow transport path 133 formed on the other side.

Here, within the control inflow transport path 133 is formed the control inflow straining protuberances 133a which protrude from the side that is in the direction of the housing frame 111 at a predetermined interval in order to form the control inflow passing paths 133b through which the liquid chemicals pass. The control inflow straining protuberances 133a are configured so that the particles as foreign object in the liquid chemicals are filtered by one of a plurality of the control inflow passing paths 133b and that the rest of the particles are filtered by the rest of the control inflow passing paths 133b when the liquid chemicals pass through the control inflow passing paths 133b. The control inflow straining protuberances 133a are provided in order to remove any particles which can be produced in the liquid chemicals temporarily stored in the control inflow space 132.

In other words, the control inflow straining protuberances 133a protrude forming a plurality of the control inflow passing paths 133b, the liquid chemicals are supplied with the particles contained in them removed in each of the control inflow passing paths 133b, thereby limiting obstruction.

On the other side of the flow rate control path 134 is formed the control outflow transport path 135 through which the liquid chemicals whose flow rate has been controlled are transported while on the other side of the control outflow transport path 135 is formed the control outflow space 136, which is located at the outflow hole 113 of the housing frame 111 and temporarily stores the liquid chemicals at the location where the liquid chemicals whose flow rate has been controlled are leaked.

Here, the control outflow transport path 135 has inside the control outflow transport path 135, on the side that is in the direction of the housing frame 111, the control outflow straining protuberances 135a at a plurality of sites at a predetermined interval so that the control outflow transport path 135 has the control outflow passing path 135b through which the liquid chemicals pass. The control outflow straining protuberances 135a are configured so that the particles as foreign object contained in the liquid chemicals transported from the control outflow transport path 135 are filtered by one of the control outflow passing paths 135b and that the rest of the particles are filtered by the rest of the control outflow passing paths 135b when the liquid chemicals are transported.

The control support unit 140 is placed on the opposite side of the housing frame 111 and includes the support frame 141 and the support protuberance 144, which are combined so that the control support unit 140 maintains hermeticity when the control support unit 140 has the flow rate control unit 130 within itself. The support frame 141 is deployed on the other side of the housing frame 111 and combined with the other side of the housing frame 111 for maintaining hermeticity inside them. Inside the support frame 141 is formed the control insertion space 142 into which the flow rate control frame 131 is inserted for maintaining hermeticity.

In addition, the support insertion groove 143, into which the insertion protrusion is inserted, is formed along the outer circumference of the control insertion space 142 with a predetermined clearance in the support frame 141 as if the support insertion groove 143 encircles the control insertion space 142. Hermeticity is enhanced by inserting the insertion protrusion 114 into the support insertion groove 143 with the control insertion space 142 inserted inside the flow rate control frame 131 when the support frame 141 is combined with the housing frame 111.

The support protuberance 144 protrudes towards one side inside the support frame 141 to be inserted into the leak prevention groove 116, which is formed on the other side of the insertion protrusion 114 to be inserted into the support insertion groove 143 in order to prevent the liquid chemicals from being leaked outside when the housing frame 111 is inserted to be combined.

The present invention has been described so far with reference to embodiments of the present invention. A person skilled in the art may acknowledge that the present invention may be achieved into various modifications within the basic features of the present invention. Therefore, the embodiments so far disclosed must be considered explicative, not definitive. The scope of the present invention is clear in the scope of Claims, not in the description that has been so far stated and all the differences within the scope of the equivalents must be interpreted to be included in the present disclosure.

REFERENCE CHARACTERS

100: Control device
110: Housing unit
111: Housing frame
112: Inflow hole
113: Outflow hole
114: Insertion protrusion
115: Control space
116: Leak prevention groove 117: Inflow conduit
118: Outflow conduit
120: Control unit
121: Control frame
122: Housing accepting groove
123: Leak prevention protuberance
124: Inflow space
125: Inflow transport path
125a: Inflow straining protuberances
125b: Inflow passing path
126: Control path
126a: Linear parts
126b: Connecting curved parts
127: Outflow transport path
127a: Outflow straining protuberances
127b: Outflow passing path
128: Outflow space
130: Flow rate control unit
131. Flow rate control frame
132: Control inflow space
133: Control inflow transport path
133a: Control inflow straining protuberances
133b: Control inflow passing path
134: Flow rate control path
134a: Control linear parts
134b: Control connecting curved parts
135: Control outflow transport path
135a: Control outflow straining protuberances
135b: Control outflow passing path
136: Control outflow space
140: Control support unit
141: Support frame
142: Control insertion space
143: Support insertion groove
144: Support protuberance

What is claimed is:

1. A flow rate control device for supplying liquid chemicals comprising:
a housing unit which is placed at a location from which liquid chemicals are supplied and comprises an inflow conduit on one side to which the liquid chemicals flow in and an outflow conduit from which flowed-in liquid chemicals whose flow rate is controlled flow out; and
a control unit which is integrated with the housing unit and comprises a control path which is connected to the inflow conduit and the outflow conduit to control the flow rate of the flowed-in liquid chemicals,
wherein on a side of the control path is formed an outflow transport path through which the liquid chemicals whose flow rate has been controlled are transported, and
wherein, the outflow transport path has outflow straining protuberances at a plurality of sites at a predetermined interval so that the outflow transport path has a plurality of outflow passing paths through which the liquid chemicals pass, and
wherein the outflow straining protuberances are configured so that foreign object particles contained in the liquid chemicals transported from the outflow transport path are filtered by one of the outflow passing paths and that particles are filtered by outflow passing paths other than the one of the outflow passing paths when the liquid chemicals are transported.

2. The flow rate control device for supplying liquid chemicals of claim 1, wherein the housing unit further comprises an insertion protrusion which protrudes from one side so that the housing unit is fastened to the control unit, has a control space in which the control path of the control unit is inserted and has a leak prevention groove on another side which assumes a shape of a groove and is inserted into the control unit so that hermeticity is maintained.

3. The flow rate control device for supplying liquid chemicals of claim 1, wherein the control unit comprises:
a control frame having a housing accepting groove along an outer circumference around the control path, which assumes a shape of a groove, into which a protruding portion of the housing unit is inserted so that the housing unit is secured in order to prevent the liquid chemicals supplied via the control path from being leaked; and
a leak prevention protuberance which protrudes from inside the housing accepting groove and is inserted into and integrated with the housing unit in order to prevent the liquid chemicals through the control path from being leaked outside.

4. The flow rate control device for supplying liquid chemicals of claim 3, wherein the control path is arranged so that an inflow hole and an outflow hole are connected thereto and placed in a zigzag pattern so that a flow path having a predesigned diameter for the flowed-in liquid chemicals to flow at a prespecified flow rate is formed up to a predesigned length.

5. The flow rate control device for supplying liquid chemicals of claim 3, wherein, inside the control frame, an inflow space to which the liquid chemicals flow in from the housing unit is formed; the control path is formed from the inflow space via an inflow transport path in a zigzag way to control flow rates; and
an outflow space is formed off which the liquid chemicals flow out to the housing unit from the control path via an outflow transport path.

6. The flow rate control device for supplying liquid chemicals of claim 5, further comprising inflow staining protuberances which protrude at a plurality of sites so that a plurality of inflow passing paths are formed inside the inflow transport path at a predetermined interval and filter particles contained in the liquid chemicals transported from the inflow transport path in order to remove the particles.

* * * * *